US012564673B2

(12) United States Patent
    Moore

(10) Patent No.: US 12,564,673 B2
(45) Date of Patent: Mar. 3, 2026

(54) SLACK RELEASE SYSTEM FOR MEDICAL TUBING

(71) Applicant: Dauntless Innovations, LLC, Germantown, TN (US)

(72) Inventor: Jesse G. Moore, Germantown, TN (US)

(73) Assignee: Dauntless Innovations, LLC, Germantown, TN (US)

( * ) Notice: Subject to any disclaimer, the term of this patent is extended or adjusted under 35 U.S.C. 154(b) by 952 days.

(21) Appl. No.: 17/522,860

(22) Filed: Nov. 9, 2021

(65) Prior Publication Data

US 2022/0143301 A1    May 12, 2022

Related U.S. Application Data

(60) Provisional application No. 63/112,123, filed on Nov. 10, 2020.

(51) Int. Cl.
    *A61M 5/14*      (2006.01)
    *A61M 5/168*     (2006.01)

(52) U.S. Cl.
    CPC ........ *A61M 5/1418* (2013.01); *A61M 5/1415* (2013.01); *A61M 5/16831* (2013.01); *A61M 2005/16863* (2013.01); *A61M 2205/18* (2013.01); *A61M 2205/3334* (2013.01); *A61M 2205/583* (2013.01)

(58) Field of Classification Search
    CPC .............. A61M 39/28; A61M 39/281; A61M 39/0208; A61M 2005/16868; A61M 5/1417; A61M 2025/024; A61M 39/26; A61M 2039/263; A61M 2039/1061; A61M 2039/1027; A61M 39/619; A61M 2205/14; A61M 5/1414–1418; A61M 2205/18; A61M 25/02; F16L 3/08–137; F16B 2/20; F16B 2/22; F16B 2/24; F16B 2/248; Y10S 128/06
    USPC ..................... 604/250, 34; 606/157; 248/339
    See application file for complete search history.

(56) References Cited

U.S. PATENT DOCUMENTS

| | | | |
|---|---|---|---|
| 2,855,173 A | 10/1958 | Treptow | |
| 2,889,848 A | 6/1959 | Redmer | |
| 2,995,334 A | 8/1961 | Henderson et al. | |

(Continued)

FOREIGN PATENT DOCUMENTS

| | | | |
|---|---|---|---|
| CN | 112043906 A | * 12/2020 | |
| GB | 2510886 A | 8/2014 | |

(Continued)

OTHER PUBLICATIONS

English text CN-112043906-A (Year: 2020).*

*Primary Examiner* — Jason E Flick
*Assistant Examiner* — Isabella S North
(74) *Attorney, Agent, or Firm* — Meunier Carlin & Curfman LLC

(57)                ABSTRACT

A medical tube management system, kit, and method of use; including a fastener, a length of tubing, and a releasable spring to retain and release slack in the tubing when accidentally tugged. The fastener being universal and interchangeable, able to connect various springs. The spring is capable of reversibly restricting flow in the tubing when uncoupled from the fastener. The fastener is capable of notifying the patient, or care taker, when the system has been tugged into the uncoupled position.

10 Claims, 10 Drawing Sheets

(56)        References Cited

U.S. PATENT DOCUMENTS

| | | | |
|---|---|---|---|
| 3,204,636 A | 9/1965 | Kariher et al. |
| 3,382,545 A | 5/1968 | Spenner |
| 3,421,187 A | 1/1969 | Ryder |
| 3,521,332 A | 7/1970 | Kramer |
| 3,616,497 A | 11/1971 | Esposito |
| 3,636,595 A | 1/1972 | Wines |
| 3,675,275 A | 7/1972 | Arblaster |
| 3,713,622 A | 1/1973 | Dinger |
| 3,874,042 A | 4/1975 | Eddleman et al. |
| 3,882,915 A * | 5/1975 | Filipski ................... A45C 1/06 |
| | | 150/134 |
| 3,984,081 A | 10/1976 | Hoganson |
| 4,219,177 A | 8/1980 | O'Day |
| 4,382,453 A | 5/1983 | Bujan et al. |
| 4,390,019 A | 6/1983 | Leveen et al. |
| 4,406,042 A * | 9/1983 | McPhee ................ F16G 11/103 |
| | | 24/130 |
| 4,406,440 A | 9/1983 | Kulle et al. |
| 4,407,472 A | 10/1983 | Beck |
| 4,453,933 A | 6/1984 | Speaker |
| 4,560,378 A | 12/1985 | Weiland |
| 4,666,111 A | 5/1987 | Schuler |
| 4,707,906 A | 11/1987 | Posey |
| 4,827,977 A | 5/1989 | Fink |
| 4,829,999 A | 5/1989 | Auth |
| 4,846,794 A | 7/1989 | Hertzer |
| 5,163,923 A | 11/1992 | Donawick et al. |
| 5,192,275 A | 3/1993 | Burns |
| 5,226,892 A | 7/1993 | Boswell |
| 5,309,604 A | 5/1994 | Poulsen |
| 5,316,246 A | 5/1994 | Scott et al. |
| 5,328,487 A | 7/1994 | Starchevich |
| 5,336,179 A | 8/1994 | Ryan |
| 5,389,082 A | 2/1995 | Baugues |
| 5,443,460 A | 8/1995 | Miklusek |
| 5,496,283 A | 3/1996 | Alexander |
| 5,507,460 A * | 4/1996 | Schneider ............... F16L 3/223 |
| | | 24/601.2 |
| 5,555,607 A | 9/1996 | Parveris |
| 5,810,323 A | 9/1998 | Winterer et al. |
| 5,820,614 A | 10/1998 | Erskine et al. |
| 5,921,969 A | 7/1999 | Vallelunga et al. |
| 6,393,675 B1 | 5/2002 | Gaetke |
| 6,546,947 B2 | 4/2003 | Abrams |
| 6,749,591 B1 * | 6/2004 | McNally ............. A61M 39/286 |
| | | 248/68.1 |
| 6,872,758 B2 | 3/2005 | Simpson et al. |
| 7,124,996 B2 | 10/2006 | Clarke et al. |
| 7,413,561 B2 | 8/2008 | Raulerson et al. |
| 7,805,978 B2 * | 10/2010 | Riley ................. G01N 29/2468 |
| | | 73/19.03 |
| 7,922,700 B2 | 4/2011 | Evans et al. |
| 7,951,092 B2 | 5/2011 | Jones et al. |
| 8,016,792 B2 | 9/2011 | Wright et al. |
| 8,197,447 B2 | 6/2012 | Wright |
| 8,262,639 B2 | 9/2012 | Mathias |
| 8,282,046 B2 | 10/2012 | Harding et al. |
| 8,491,543 B2 | 7/2013 | Stringham |
| 8,523,824 B2 | 9/2013 | Teirstein et al. |
| 8,562,512 B2 | 10/2013 | Menn |
| 8,584,323 B2 | 11/2013 | Pang |
| 8,746,246 B2 | 6/2014 | Lueckenhoff |
| 8,840,589 B2 | 9/2014 | Bierman et al. |
| 8,998,825 B2 | 4/2015 | Matsuno et al. |
| 9,498,616 B2 | 11/2016 | Mathias et al. |
| 9,499,318 B2 | 11/2016 | Mohika |
| 9,511,185 B2 | 12/2016 | Slaker et al. |
| 9,664,213 B2 | 5/2017 | Mohika et al. |
| 9,694,130 B2 | 7/2017 | Andino et al. |
| 9,808,573 B1 | 11/2017 | Dooley |
| 10,556,058 B2 | 2/2020 | Tamrazi et al. |
| 10,576,259 B2 | 3/2020 | Stafford |
| 10,646,648 B2 | 5/2020 | Isaacson et al. |
| 10,655,768 B2 | 5/2020 | Jones et al. |
| 10,786,652 B2 | 9/2020 | Doshi et al. |
| 10,857,346 B2 | 12/2020 | Dennis et al. |
| 10,881,782 B2 * | 1/2021 | Behrens ................... F16L 3/20 |
| 11,033,711 B2 | 6/2021 | Coatsworth et al. |
| 2002/0007538 A1 | 1/2002 | Bourgerie |
| 2002/0096608 A1 | 7/2002 | Cedarberg, III |
| 2003/0055381 A1 | 3/2003 | Wilkinson |
| 2005/0077436 A1 | 4/2005 | Nelson |
| 2006/0113432 A1 | 6/2006 | Driskell |
| 2007/0038233 A1 * | 2/2007 | Martinez ........... A61B 17/1227 |
| | | 606/157 |
| 2007/0142785 A1 | 6/2007 | Lundgaard et al. |
| 2007/0149914 A1 | 6/2007 | Axelsson et al. |
| 2007/0215759 A1 | 9/2007 | Heegaard et al. |
| 2009/0076417 A1 | 3/2009 | Jones |
| 2009/0254034 A1 | 10/2009 | Beck et al. |
| 2010/0115739 A1 | 5/2010 | Mathur |
| 2010/0152613 A1 | 6/2010 | Ryan et al. |
| 2014/0117170 A1 | 5/2014 | Sharpe et al. |
| 2014/0306070 A1 | 10/2014 | Hartsock et al. |
| 2014/0317929 A1 * | 10/2014 | Robert .............. A61M 5/14244 |
| | | 29/890.124 |
| 2014/0345111 A1 | 11/2014 | Belley et al. |
| 2015/0285404 A1 * | 10/2015 | Koyama ........... A61M 5/14228 |
| | | 248/74.2 |
| 2016/0053784 A1 | 2/2016 | Mohika et al. |
| 2016/0074628 A1 | 3/2016 | Smith et al. |
| 2017/0067586 A1 | 3/2017 | Jones et al. |
| 2019/0014676 A1 * | 1/2019 | Nakamura .............. F16B 2/245 |
| 2020/0284385 A1 | 9/2020 | Fangrow |
| 2021/0361923 A1 * | 11/2021 | Hamilton .............. A61M 39/08 |

FOREIGN PATENT DOCUMENTS

| | | |
|---|---|---|
| TW | M550293 U | 10/2017 |
| WO | 2009/110803 A1 | 9/2009 |

* cited by examiner

SLACK RELEASE SYSTEM FOR MEDICAL TUBING

CROSS-REFERENCE TO RELATED APPLICATIONS

This application claims benefit to U.S. Provisional Application Ser. No. 63/112,123, filed Nov. 10, 2020, and titled "SLACK RELEASE SYSTEM FOR PERIPHERAL INTRAVENOUS LINES," the entirety of which is incorporated herein by reference.

TECHNICAL FIELD

This disclosure relates generally to devices and methods for securement of medical tubing, and in particular to provide a breakaway system for release of tube slack to reduce the risks from accidental dislodgement.

BACKGROUND

Peripheral intravenous (PIV) and central venous access devices (CVADs), with the combination of intravenous (IV) medicines, have greatly enhanced our quality of life. They are effective, fast acting, easy to administer, and cost effective. Dosed medicines may be administered to a patient via flexible tubing, or IV lines, which are connected to a patient via the arm or another insertion site. IV tubing is often secured directly to the patient with tape, bandages, or specialty adhesive covers to form a mostly permanent installation penetrating the patient's skin. Device securement and management is required to limit complications associated with PIV and CVADs. Complications include device failure, accidental dislodgement, phlebitis, infiltration, extravasation, occlusion, and infection. A major disadvantage of intravenous setups, like those described above, is that patients who may be in a confused state of mind are prone to accidental movement which may dislodge their secured tubing, such as an IV line. IV lines may also be accidentally dislodged by caretakers, visitors, or pets. Dislodgement of the IV line consumes time for an IV restart as well as wasted costs, spilled medicines, patient complications, and additional health risks. To help improve safer use of IV lines, when accidentally tugged, the invention releases slack in the tubing to reduce the risk of dislodgement.

Clinical management of a variety of flexible tubes for patients of various sizes requires multiple sizes clamps and securement devices. The invention overcomes this problem by offering a universal fastener which can be added to an existing IV tube for gathering and retaining tubes interchangeably, and which can easily be exchanged on and off the tube or spring. The variety of springs available provides a quickly adjustable securement system for retaining different sized tubes to accommodate individual patient needs and risk factors. The universal fastener helps to reduce inventory, improve flexibility, and ease the work of caregivers.

SUMMARY

In various embodiments, a system is disclosed. The system includes a flexible IV tube extending between a patient insertion site and an IV stand. Slack in the tube is gathered and formed into a loop between the patient insertion site and the IV stand, wherein the tube is affixed to a spring at a first loop end, and the tube is affixed to the fastener at a second loop end. The spring retains the first loop end in a pocket, and the fastener retains the second loop end in an aperture. The spring is operatively attached to the fastener in a coupled position and detached in an uncoupled position.

In various embodiments, a system is disclosed. The system includes a flexible IV tube extending between a patient insertion site and an IV stand. Slack in the tube is gathered and formed into a loop between the patient insertion site and the IV stand, wherein the tube is affixed to a first spring at a first loop end, and the tube is affixed to a second spring at a second loop end. A fastener is then attached to the first spring and the second spring. The first spring retains the first loop end in a first pocket, and the second spring retains the second loop end in a second pocket. The springs are operatively attached to the fastener in a coupled position and detached in an uncoupled position.

In various embodiments, a system is disclosed. The system includes a flexible IV tube extending between a patient insertion site and an IV stand. A spring retains a segment of tube in a pocket. Slack in the tube is gathered up and the spring is operatively attached to the fastener, the fastener being attached to the IV stand. The system comprising a coupled position when the spring is attached to the fastener, and an uncoupled position when detached.

In various embodiments, a method is disclosed. The method includes a step of gathering slack in an IV line between a patient insertion site and an IV stand. The IV line is attached to one or more springs. The spring is be coupled to the fastener. When sufficient tension is applied on the IV line, the spring is uncoupled from the fastener and the slack is released. The uncoupling will be configured and arranged to notify the patient, or caretaker, that a slack releasing event has occurred; thereby indicating a need to inspect the needle insertion site integrity before re-coupling the slack release system.

In various embodiments, the fastener may include an aperture, a hook, a docking recess, or an electric circuit. The spring may include a pocket, a flow restricting pocket, a pinch tab end, a color coating, or a circuit completing member. The examples presented are intended to provide clarity regarding use with an IV line, without limiting the scope of the invention to the applicable benefits in other medical tubing and cable systems. Other medical uses of tubing systems include catheters, guide wires, nasogastric tubes, stents, cannulas, surgical drains, parenteral tubes, feeding tubes, and other conventional devices.

BRIEF DESCRIPTION OF THE DRAWINGS

The following drawings are illustrative of particular embodiments of the invention and therefore do not limit the scope of the invention. The drawings are not necessarily to scale (unless so stated) and are intended for use in conjunction with the following detailed description of preferred embodiments of the invention. Embodiments of the invention will hereinafter be considered together with the accompanying drawings, wherein like numbers denote like elements.

3

Figure 4:
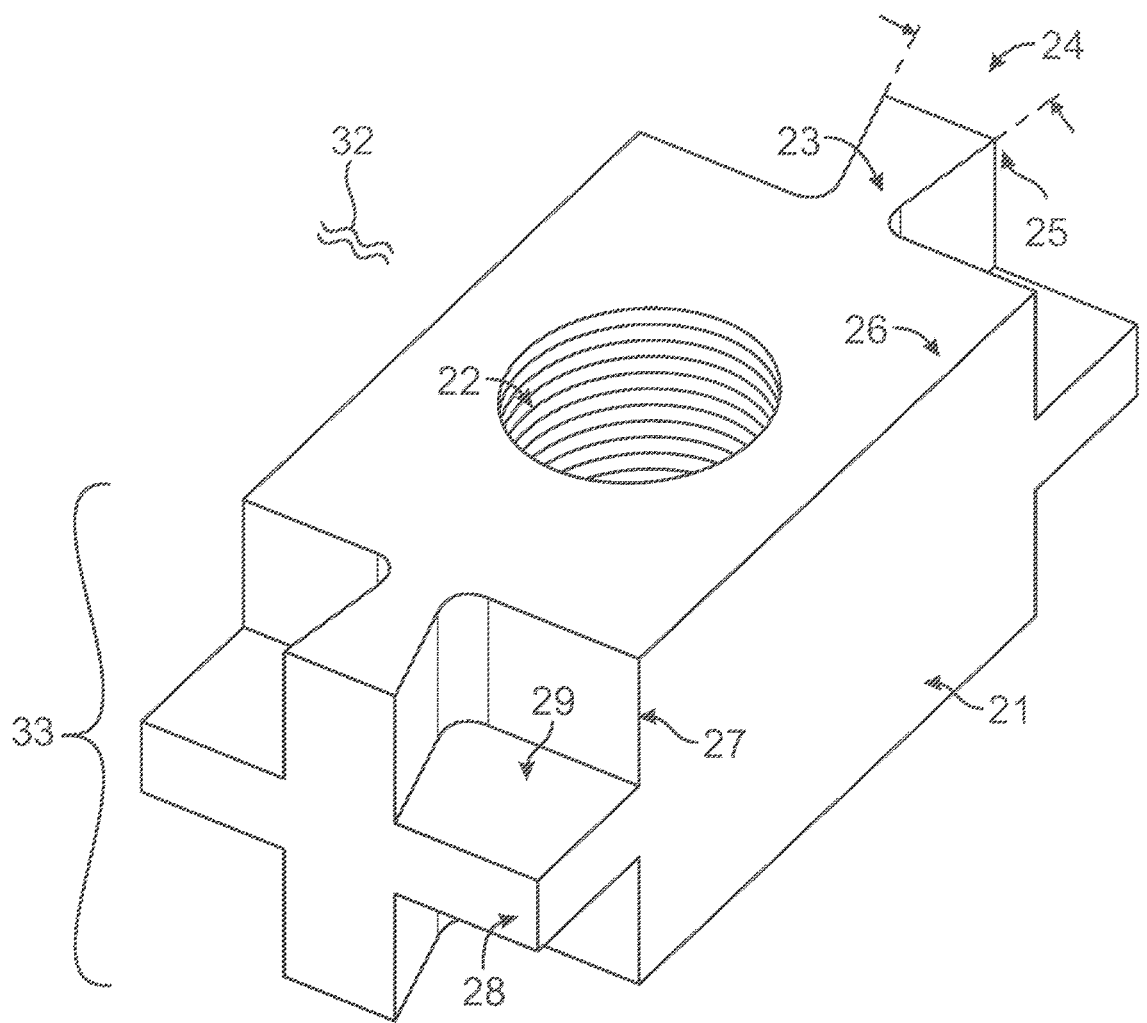
FIG. 4. illustrates a perspective view of the fastener according to an embodiment of the invention.
Figure 5:
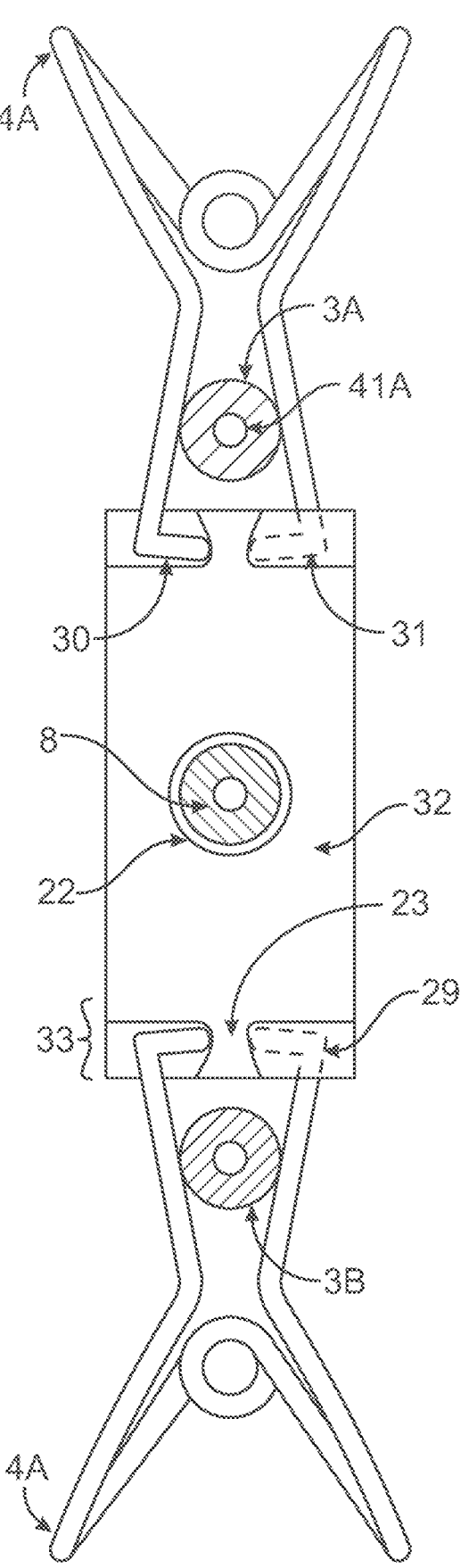
Figure 6:
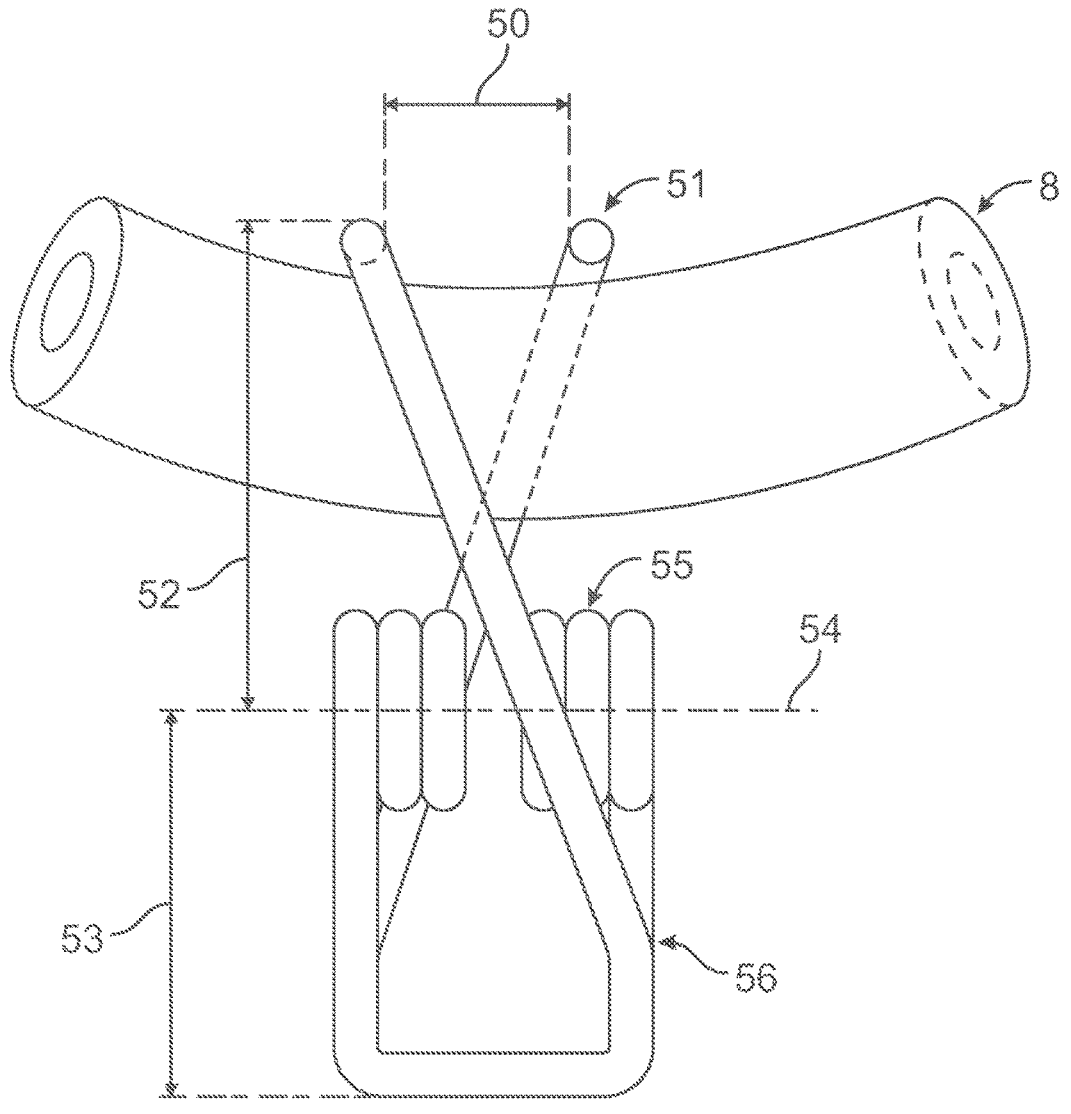
Figure 7:
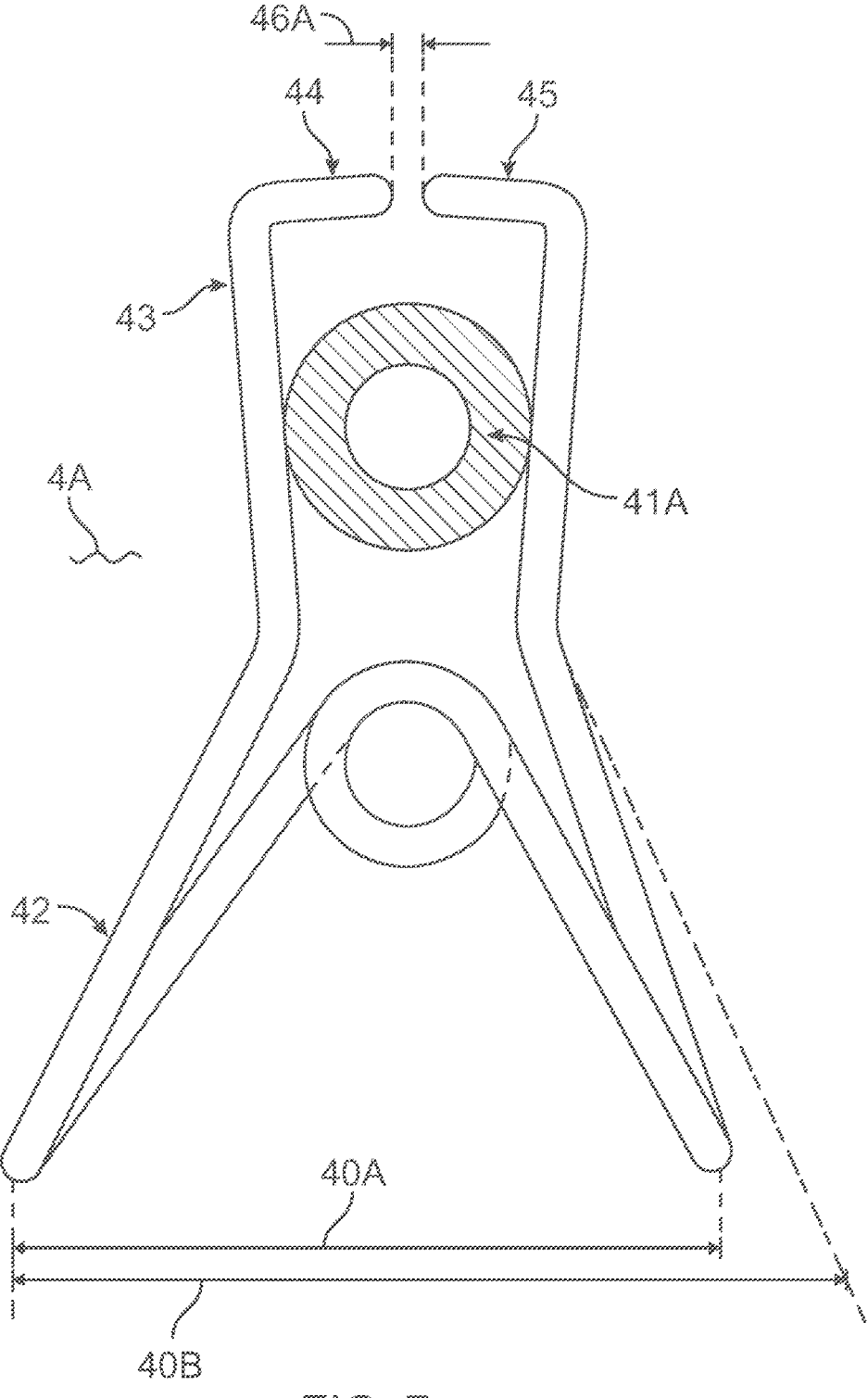
Figure 8:
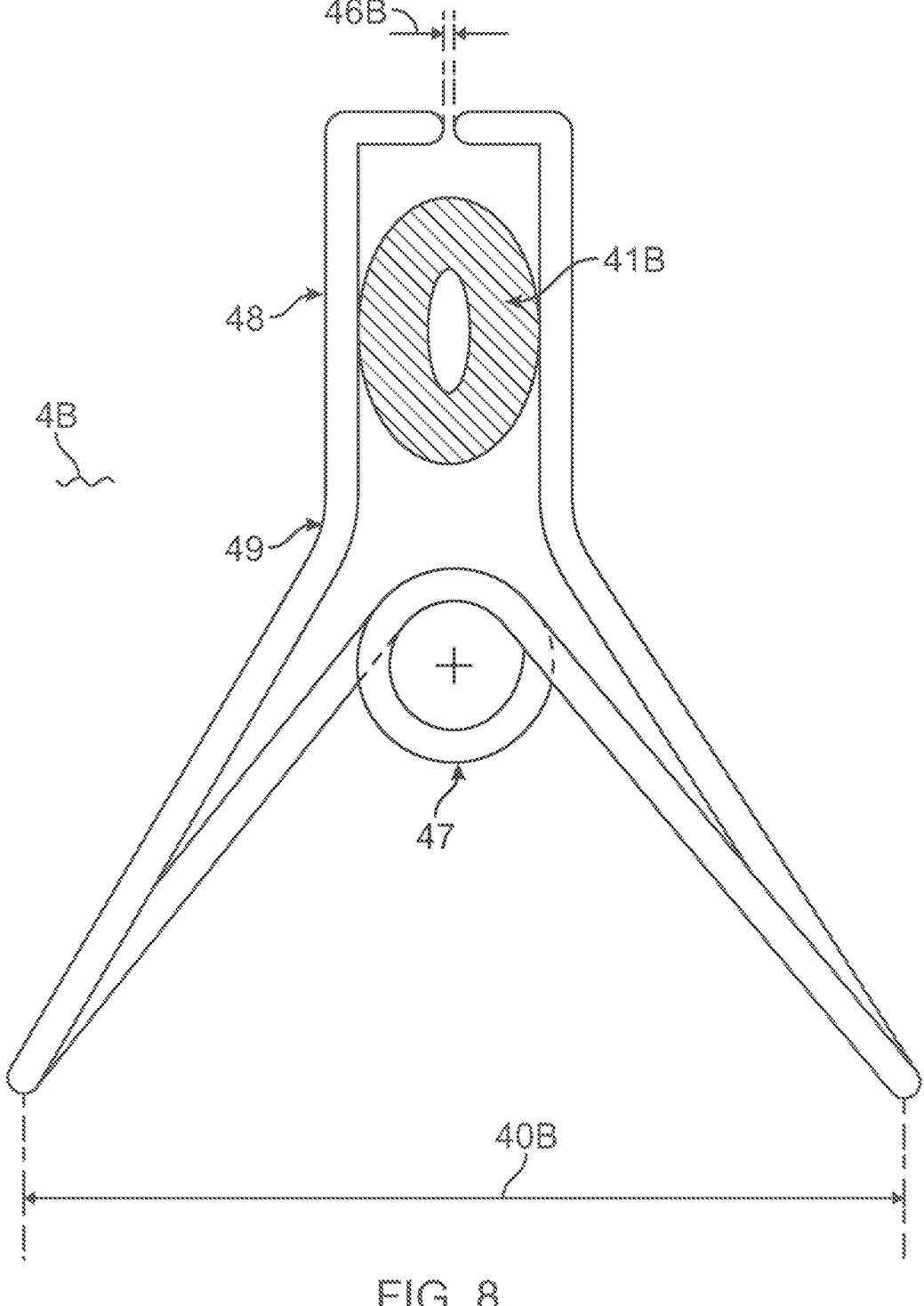
Figure 9:
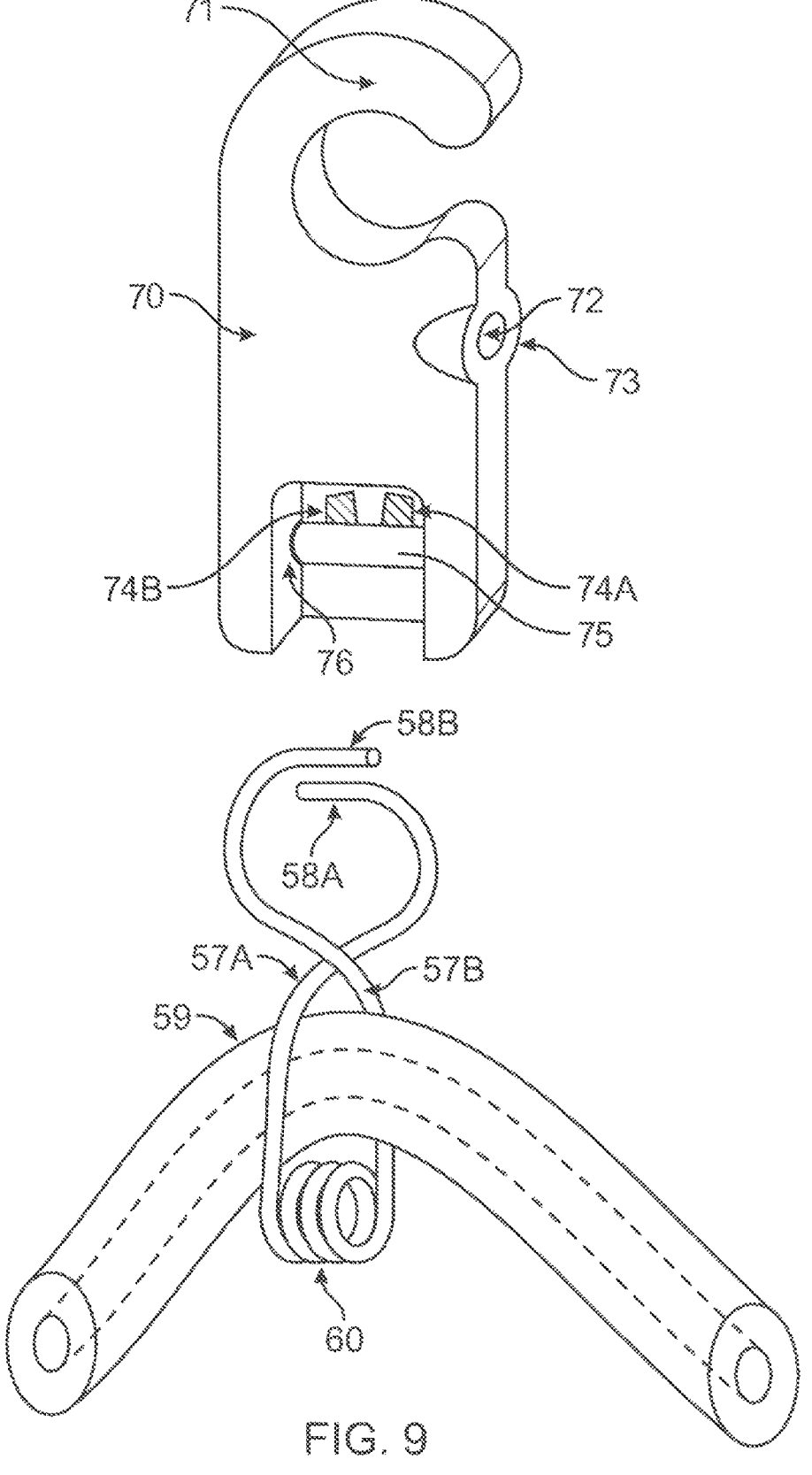
Figure 10:
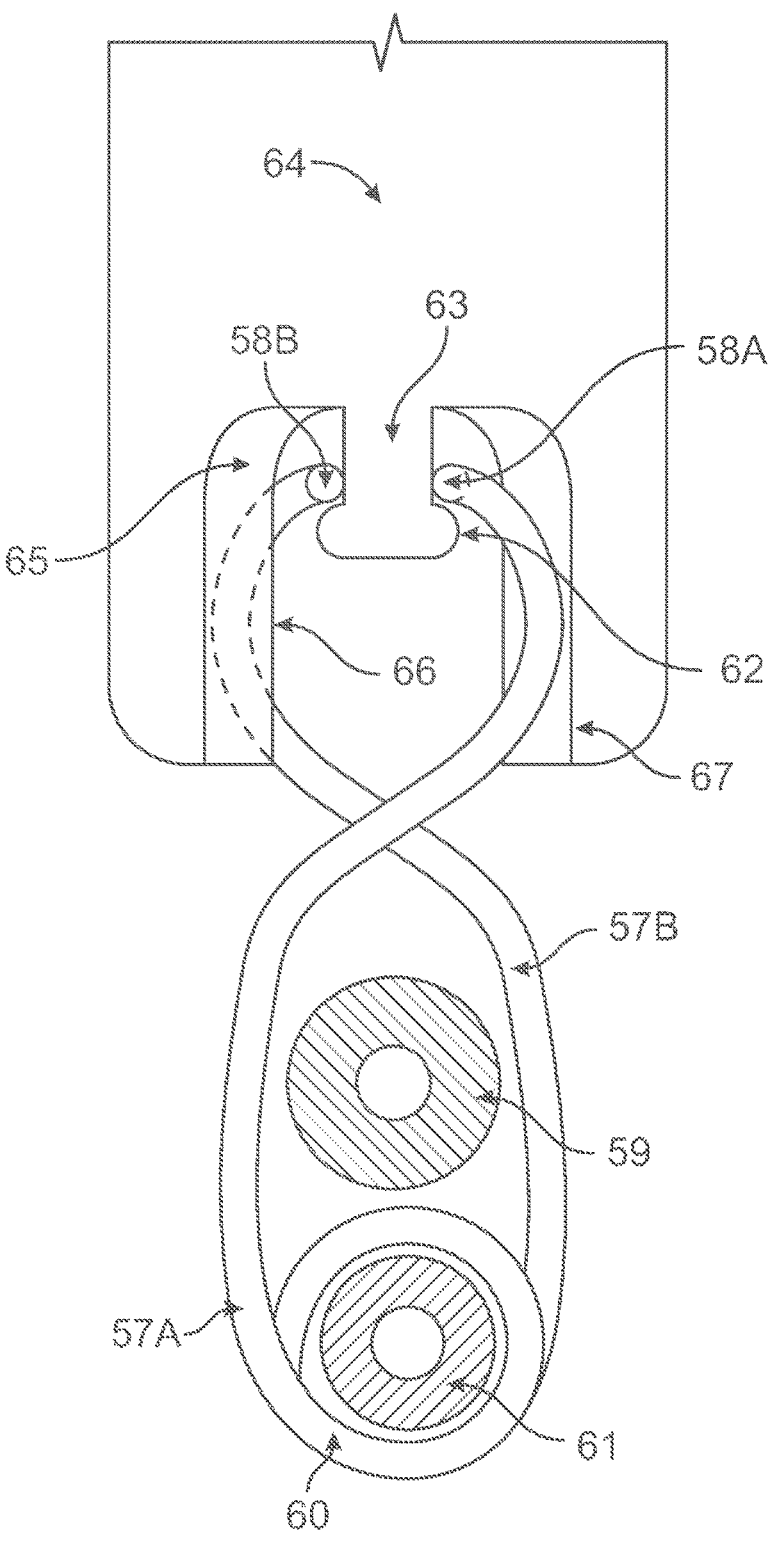

FIG. 5 illustrates a top view of the fastener shown in FIG. 4, where the system includes two coupling ends, two springs, and three segments of tubing which forms two tube loops;

FIG. 6 illustrates a side view of the spring shown in FIG. 5, where the spring is coupled to the tubing;

FIG. 7 illustrates a top view of the spring shown in FIG. 5, in a free flow position;

FIG. 8 illustrates a top view of the spring shown in FIG. 5, in a constricted flow position;

FIG. 9 illustrates a perspective view of the fastener, the spring, the electric circuit, and the tubing according to an embodiment of the invention;

FIG. 10 illustrates a detail view of the fastener, the spring, and two segments of tubing according to an embodiment of the invention;

DETAILED DESCRIPTION

This following detailed description is exemplary in nature and is not intended to limit the scope, configuration, or applicability in any way. The following embodiments are intended to be read in connection with the accompanying drawings, which are to be considered part of the entire written description. The drawing figures are not necessarily to scale and certain features may be shown exaggerated in scale or in somewhat schematic form in the interest of clarity and conciseness. Those skilled in the art will recognize that many of the noted examples have a variety of suitable alternatives and it is not necessary for all embodiments of the invention to have all the advantages of the invention or fulfill all the purposes of the invention. Relative terms used in the description should be interpreted to refer to the orientation as then described or shown. These terms are for contextual clarity and are not intended to require a particular orientation. Terms concerning attachments and the like, such as "coupled" and "coupling" refer to a relationship wherein structures are secured or attached to one another either directly or indirectly, temporarily or permanently, through intervening structures, as well as both movable or rigid attachments or relationships, unless expressly described otherwise. The term "operatively coupled" is such an attachment or connection that allows the pertinent structures to operate as intended by virtue of that relationship. As used herein, the term "substantially" denotes elements having a recited relationship (e.g., parallel, perpendicular, offset, restricted, measuring, aligned, etc.) within acceptable manufacturing tolerances. It will be recognized that greater and/or lesser deviations can exist based on manufacturing processes and/or other manufacturing requirements.

It is appreciated that the features associated with each of the embodiments of the invention are not limited to the particular embodiment for which the features are described and are combinable with features described in association with all embodiments of the invention.

Embodiments of the invention include a spring and fastener system for management of medical tubing. Practical utility includes organizing medical tubing into a position which reserves and releases slack upon accidental tugging, thus reducing the risk of injury at the patient insertion site. The slack release system provides a tactile warning before uncoupling at a threshold release force. Examples include using the system to temporarily reserve a length of flexible tubing in the operatively coupled position, which when tugged releases the spring from the fastener at a controlled threshold release force, thereby releasing the slack in the tubing and protecting the enteral insertion site of the patient. An example includes management of IV tubing where the patient insertion site includes a needle secured with tape to the patient. In another example, the tubing is a catheter. An example system includes a releasable, or temporary, capturing of slack in the tubing line and keeping it out of the way by attaching to a pole, bed, rail, or fixture in the patient's vicinity. In another embodiment, the slack is temporarily captured in a single or multiple convolution, coil, wind, wrap, or loop of tubing.

Figure 1:
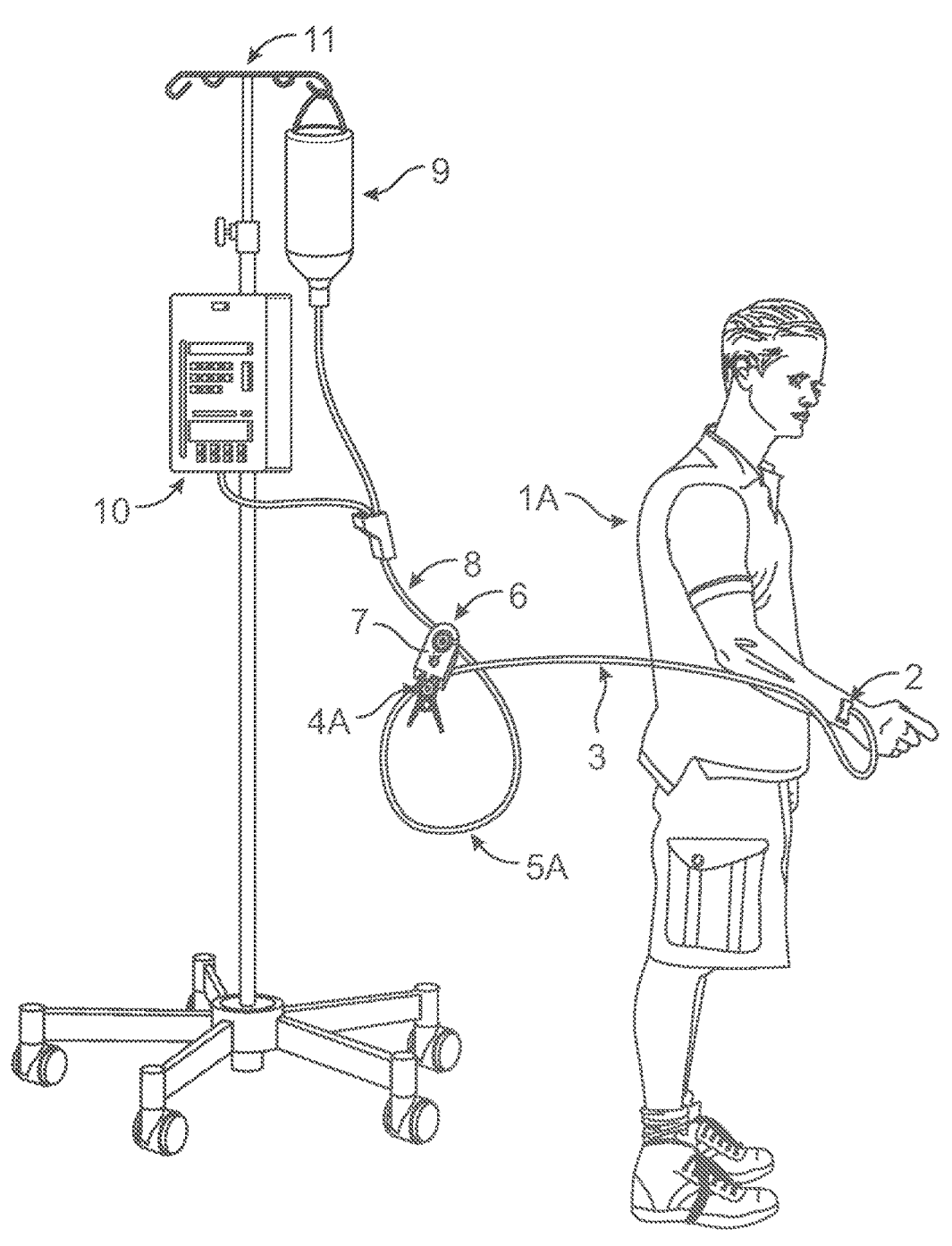
FIG. 1 illustrates a system view in the coupled state.

FIG. 1 illustrates the system as shown coupled in application with a patient in unaware motion 1A, where the IV insertion site 2 is attached to the wrist. The IV line consists of a second tube segment 3, a coupled spring 4A, a loop of tubing 5A, a fastener 6, a coupled release system 7, and a tube segment 8. The IV fluid bag 9 is hung from an IV stand 11 and includes an optional monitoring system 10. The monitoring system 10 is known to provide an occlusion, or distal blockage, alarm when fluid flow restriction is detected as defined by the monitoring system manufacturer. In another embodiment, the monitoring system 10 is not present in application of the slack release invention. In another embodiment, the IV line includes conventional features, including but not limited to a manual clamp, extension tubing, Luer-lock, connector, port, or a roller clamp.

Figure 2:
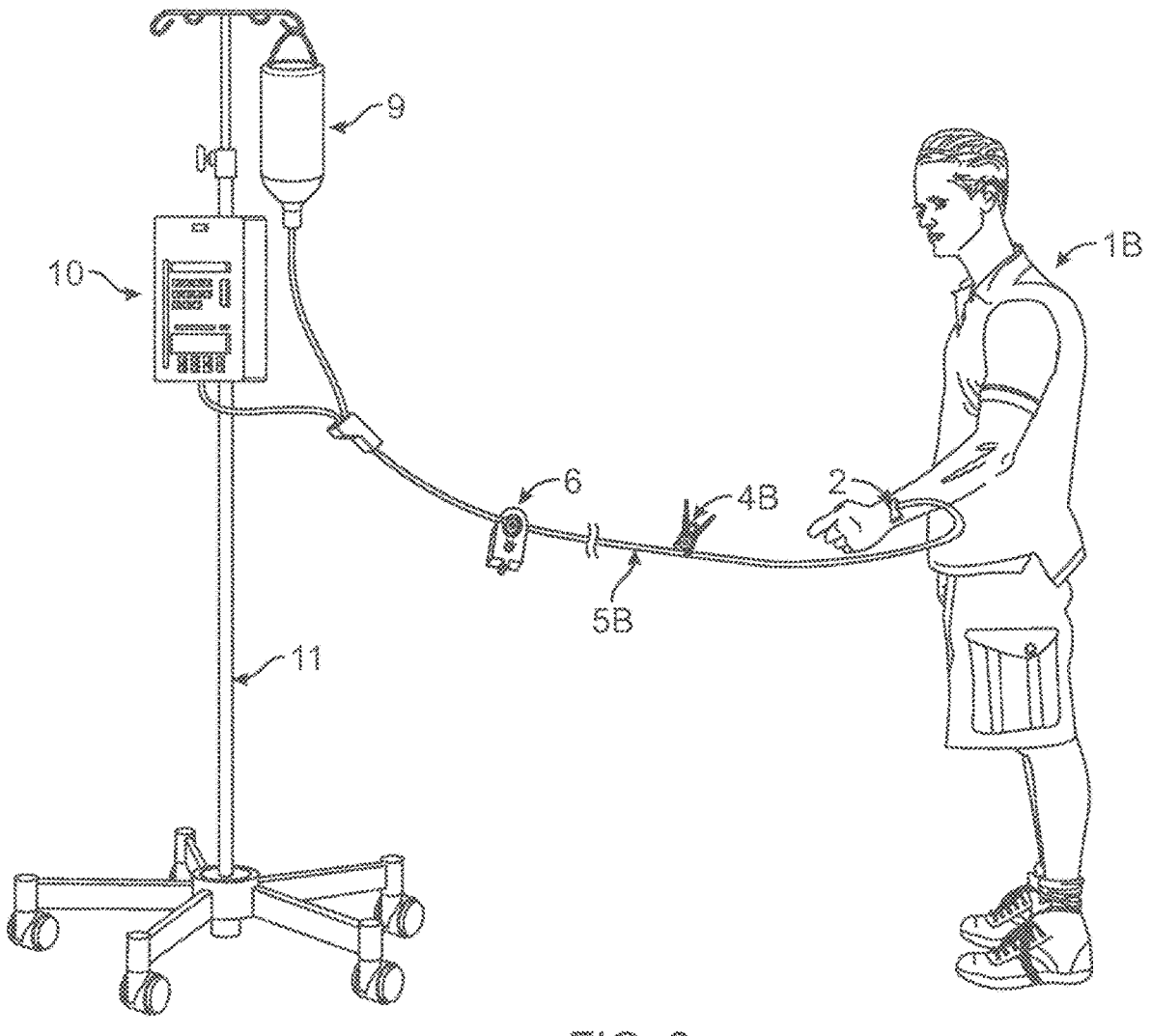
FIG. 2 illustrates a system view in the uncoupled state, where slack has been released in the tubing previously shown as reversibly coupled in FIG. 1.

FIG. 2 illustrates the system and method in an uncoupled state, wherein the patient 1B is made aware of a tugging tension while in motion, and where the IV insertion site 2 remains attached to the wrist. The loop of tubing 5A is shown to release and create slack in the length of tubing 5B. The uncoupled spring 4B is shown to releasably attach to the second tube segment 3. The length of slack that is released when the loop of tubing 5A is uncoupled from the slack length of tubing 5B is chosen and set by the caregiver, and may range from 5 inches to 12 feet, preferably from 2 feet to 5 feet. The system and method of use are capable of cycling between the coupled and uncoupled position repeatedly.

Figure 3:
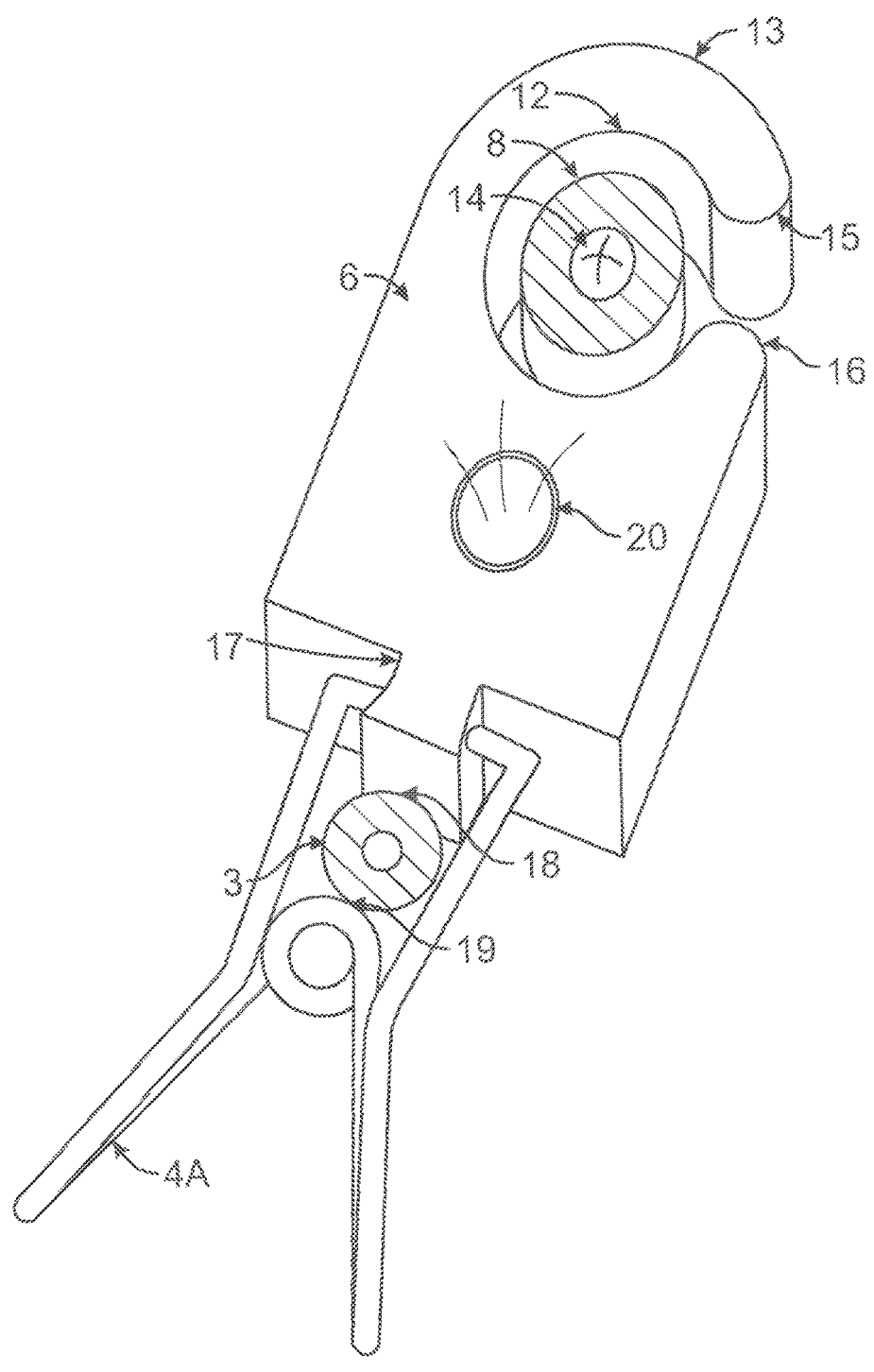
FIG. 3 illustrates a top view of the system shown in FIG. 2, where the tubing is retained within both the fastener and spring according to an embodiment of the invention.

FIG. 3 illustrates the fastener 6, as a mounting bracket, to be attached to the tube segment 8. The tube segment 8 consists of at least one lumen 14 forming an axis of the flexible tube with a conventional outer diameter which ranges from, but is not limited to, Ø0.3 mm to Ø30 mm, with an inner diameter of Ø0.1 to Ø28 mm. Medical tubing, or tubing, is conventionally known to be flexible and made from a resilient polymer material which is capable of being reversibly clamped, constricted, or pinched in medical applications where intermittent restriction of fluid flow is desired. In this embodiment, the aperture 12 is sized and arranged to fit a preferred IV tubing size with an outer diameter ranging from Ø1 mm to Ø8 mm. In this example, the aperture 12 forms a hook 13 and includes a gap formed by a far end 15 and near end 16, configured and arranged to allow ingress and egress of the tube segment 8 to and from the aperture, and whereby connecting, snapping, or affixing the tube to the fastener. In one embodiment, the tube segment 8 has a substantial outer diameter of Ø5 mm, the gap width is 2.5 mm, and the aperture 12 is Ø4.9 mm. Sizing of the fit between the tube segment 8 and aperture 12 ranges from a snug interference fit to a non-interference sliding fit. In this embodiment, the fastener 6 is fitted onto a tube segment 8 at any position along the length of tube that suits the user and does not require preassembly of the fastener onto the tubing. The aperture 12 is sized and arranged so that fluid flow through the lumen 14 is not substantially restricted when the tube segment 8 is affixed to the aperture 12 in the coupled or uncoupled position. The fastener 6 and spring 4A may be manufactured from plastic, metal, wood, or any suitable material or combination therein. In a preferred embodiment, the spring 4A is made of stainless spring steel and the fastener 6 is made of an injection molded ABS plastic. In another embodiment, the fastener may be formed from any suitable material, including nylon, plastic, or polymer of varied colors. Alternative spring materials include, but are not limited to, piano wire, brass wire, or flat stamped spring steel which are combined with metal wire loops known as paper binder clips. The spring is configured and arranged to operate within the material range of elastic deformation. Processes for conventional construction may include, but are not limited to, injection molding, over-molding, wire bending, wire winding (hot or cold), stamping, extrusion, and machining.

In another embodiment, the fastener 6 comprising a hook 13, is configured and arranged to attach to an IV tube stand 11, bed rail, textile, or any other surface in the patient's vicinity. In this embodiment, the second tube segment 3 is affixed to the coupled release system 7 with a coupled spring 4A, wherein tube slack is collected by hanging the hook 13 to be draped up and out of the way.

As further shown in FIG. 3, a coupled spring 4A is shown in a loaded position and operatively coupled to a docking tab neck 17 integral to the fastener 6. The second tube segment 3 is configured and arranged to nest within a pocket, including a spring contact point 19 in the coupled position of the coupled release system 7. Sizing of the fit between the second tube segment 3 and the coupled spring 4A ranges between an interference fit and a non-interference fit. In one embodiment, the coupled release system 7 should not easily slide along the second tube segment 3 unless the spring is opened and readjusted to a new position along the tubing. In another embodiment, the pocket is formed by a plurality of spring contact points 19. In another embodiment, the pocket includes a fastener contact point 18.

As further shown in FIG. 3, an indicator 20 is incorporated into the fastener. The indicator includes an electronic circuit that illuminates an LED light, triggers an audible sound, or notifies a wireless computing device to notify a user when the system has been uncoupled.

FIG. 4 illustrates an embodiment of the fastener 21 with two symmetric docking ends 33 including reference features 23, 24, 25, 27, 28, and 29; and also an aperture in the form of a though hole 22. The through hole 22 includes a texturing along the through hole 22 to optimize the desired fit between tubing 8 and the fastener body 32. An example of texturing includes a knurl, molded roughness, ribs, or any other conventional technology. The fastener body 32 includes a top face 26 and a side face 21. In this embodiment, the docking end 33 includes a recess edge 27 offset from a docking end surface 28. The docking end surface 28 includes a partition surface 29 which divides the docking end horizontally. The docking end 33 is divided vertically by an angled tab 23. The docking end surface 28 is offset from the recess edge 27. The angle 24 is tapered to create a ramp of resistance to a spring surface. The resulting span of the ridge width 25 is sized and configured to match a desired spring clamp force comprising a controlled threshold release force designated to uncouple the system. The ridge width 25 is a substantial size which is designed to communicate with a coupled spring 4A. In this embodiment, the features are symmetric and balanced in weight distribution. In another embodiment, the features are asymmetric and unbalanced in weight distribution. In another embodiment, the docking ends 33 extend from the fastener 21 at a variety of angles relative to one another. In another embodiment, the fastener's docking end 33 comprises two blind holes configured and arranged to receive two ends of a coupled spring 4A at a depth and angle capable of retaining the spring in a coupled position. The docking end 33 comprising a textured surface to communicate with the coupled spring 4A with a conventional frictional coefficient. In another embodiment, the side face 21 width is not consistent throughout the fastener and is narrower in the aperture 12 region and thicker in the docking end 33 region.

As further shown in FIG. 4, in another embodiment the fastener 21 may include a plurality of apertures 12 that consist of a through hole 22 and/or a hook 13 configuration. In this example, the aperture is used for mounting to an IV stand 11, bed rail, or additional segments of tubing. In another embodiment, the aperture 22 is removed.

FIG. 5 illustrates a slack release system, with two coupled springs 4A attached to the fastener 32. In this embodiment, there are two docking ends 33 including an angled tab 23 and a partition surface 29 in a coupled position where the flow is not restricted through the free flowing tube 41A. The tube segment 8 is slidably contained within the aperture 22 where it can be pulled by hand along the axis of the tube and is configured and arranged to sufficiently bind the tube onto the fastener 32 to allow uncoupling when the tube is tugged in the direction of the insertion site 2 or the IV stand 11. The springs 4A are coupled to the fastener 32 at opposing left jaw 30 and right jaw 31. In this embodiment, the left jaw 30 and right jaw 31 are spaced in an open position when docked to abut the angled tab 23 and partition surface 29. In this example, the partition surface 29 helps to ensure the uncoupling of the spring is achieved by a pulling motion, overcoming the ridge width 25 and communicating spring 4A force, rather than twisting off at a lower value. The spring 4A is retained within a pocket between the left jaw 30 and right jaw 31. The springs 4A are shown to releasably capture a tube segment 3A and 3B. The tube segment 3A is shown to be the same size as tube segment 8 and 3B; wherein it represents a double loop of the same tube segment. In another embodiment, the tube segment 3A is a second tubing with a different diameter, operatively coupled to the same fastener 32 with tube segment 3B. In another embodiment, the tube segment 8 is press fit into the aperture 22 where it cannot be slidably adjusted by hand along the axis of the tube.

As further shown in FIG. 5, the ridge width 25 is sized and configured to correspond to a desired torsional spring load, torsion moment, and spring constant rate which is known in the art of torsion spring design. The spring load corresponds to the controlled threshold release force. In a preferred embodiment for an adult patient, the coupled position utilizes a spring diameter of 1.2 mm and is configured to achieve a load, or spring force, substantially measuring 20 pounds. In an alternate embodiment for a child patient, the coupled position utilizes a spring diameter of 0.7 mm and is configured to achieve a spring force, substantially measuring 10 pounds. In another embodiment a heavy spring utilizes a 2 mm spring diameter. Overcoming the spring force is achieved with a tugging motion and results in transitioning the system from the coupled position in FIG. 1, to the uncoupled position in FIG. 2. In another embodiment, the coupled spring load force, or clamping pressure, falls within a range from 2 to 100 pounds. In this embodiment, the strength of connection between the aperture 12 and tube segment 8 interface will be configured and arranged to connect with a strength that exceeds the coupled spring 4A force, thereby first uncoupling at the spring 4A and docking end 33 interface when the system is tugged.

As further shown in FIG. 5, the springs 4A are shown to be the same size. In another embodiment, the springs are of different sizes and strengths which are configured and arranged to retain a different diameter tubing and clamping pressures. A plurality of docking ends 33 remain universal, with a consistent size and arrangement, to receive any spring stiffness and size which is configured and arranged to operatively couple to the docking end 33 of the fastener 32. The variability in spring offerings correspond to a color coated plastic, anodization, surface treatment, or paint to visually indicate sizes. In one embodiment, a green spring fits a micro-drip set for a flow rate, or drop factor, of 60 drops/mil tube. Further, a blue spring is for a macro-drip set of 20 gtts/mL tube size and a red spring is for a macro-drip set of 10 gtts/mL tube size. In another embodiment color coating of the spring 4A and additionally identify a flow constricting, or restricting, spring as white and non-restricting spring as uncoated metal. In the medical arts, offering a universal docking end 33 to accept a varied range of spring 4A sizes will provide convenience and adaptability in use of multiple tube segment 8 diameters and materials.

FIG. 6 illustrates a side view of a double wound spring coil 55 configured about a torsion spring axis 54 with mouth segment 52 and pinch tab segment 53. In this embodiment, the spring end 51 wraps around the tube segment 8 opposite the torsional axis 54; which will hug and retain the tubing within the mouth segment 52. The mouth width 50 is sized to allow the selected diameter of tubing to squeeze between the arms of the spring mouth segment 52, making it possible to attach the spring to an existing tube segment 8 and avoiding the need for pre-assembly. Capturing the tube segment 8 within the spring is achieved by twisting the spring axis 54 perpendicular to the tube segment 8 for ingress and egress. Once captured, the spring can be rotated to the position shown in FIG. 6.

As further shown in FIG. 6, this embodiment includes a bend 56 to create a crossing pattern to clamp, or pinch, the tube segment 8 and restrict flow in the tube segment 8. In another embodiment, the mouth segment 52 consists of spring arms 43 which are bent to align in parallel in the side view from additional bends 56 in opposing directions. The spring arms 43 in the uncoupled position comprising a clamping configuration to restrict flow in the tube segment 8.

As further shown in FIG. 6, the spring ends 51 terminate on the mouth segment 52. In another embodiment, the spring ends 51 terminate on the pinch tab segment 53; maintaining a continuous section of wire in the mouth segment 52. In another embodiment, variations of bends, coils, lever arm length, wire end points, and spring rates may be designed to suit each tube size with desired fit and clamping force using conventional spring manufacturing techniques. The spring including features that cooperate with a universal docking end.

FIG. 7 illustrates a top view of a coupled spring position 4A, wherein the left end 44 and right end 45 form a coupled gap 46A. In this embodiment, the opposing spring left end 44 and right end 45 are long enough to retain the free flowing tube 41A within the coupled gap 46A. The coupled position provides that the spring arms 43 do not compress the free flowing tube 41A. The pinch tab arms 42 squeeze between an arm coupled position 40A and an uncoupled position 40B. The spring arm positions will fall within the range of human hand grip and preferably transition from one inch in the coupled position 40A to two inches in the uncoupled position 4B. In another embodiment, the coupled position 40A is an eighth of an inch and the uncoupled position 40B is three inches. Variation on the travel, or throw, of the spring between coupled and uncoupled position is configured to suit various tube sizes and materials. In another embodiment, the spring 4A is affixed to a pair of operatively coupled arm extensions whereby extending the length of the spring lever arm away from the spring axis 54 and toward the mouth segment 52 or the pinch tab segment 53. Arm extensions may be made of wood, plastic, or metal. The arm extensions, in cooperation with the spring 4A and 4B, form a retention pocket for the free flowing tube 41A and are configured and arranged to couple to the fastener 32. In one embodiment, the arm extensions comprise the retention pocket with tube outer surface contacts the inner surface of the arm extension mouth segment in the coupled and uncoupled position. In another embodiment, the arm extensions are configured to restrict fluid flow in the tube when in the uncoupled position.

FIG. 8 illustrates a top view of an uncoupled spring position 4B. The spring coil 47 is wound to achieve a free position which forms a compressed tube 41B in a flow restricted state. The free position for a spring is understood in the art to refer to a starting, unloaded, natural, or resting position. The compressed tube 41B is not sealed, but reversibly pinched tight. A flow restricted state is sufficient to trigger an alarm when a monitoring system 10 is utilized as shown in FIG. 2. In a preferred embodiment, a restricted flow in an IV tube designated for 60 drops/mil flow is substantially restricted to 1% at 0.6 drops/mil. In another embodiment, the flow through a tube is substantially restricted in a range from 0.001% to 75% of the tube's designated flow rate. It is appreciated by those skilled in the art that fluid flow in IV lines is a function of tube length, tube radius, pressure, flow rate, and fluid viscosity; which is characterized by Poiseuille's Equation. In this embodiment, the unrestricted flow, or allowed flow condition in the tube is understood to have inherent restrictions with changes in the flexible IV line. In another embodiment, it is understood that the "unrestricted flow" designates substantially less than 50% restriction of flow, of which is attributed to the slack release system.

As further shown in FIG. 8, the uncoupled gap 46B is shown as smaller than the coupled gap 46A. In another embodiment, the uncoupled gap 46B is zero where the left end 44 and right end 45 contact one another. In another embodiment, the uncoupled gap 46B is negative, where the left end 44 and right end 45 pass one another in the direction of the spring's free position.

As further shown in FIG. 8, a side bend 49 is formed in the spring on the mouth side 52 of the spring axis 54, resulting in parallel mouth segment arms 48 which are substantially parallel when in the spring uncoupled position 40B; and flow is restricted in the compressed tube 41B. In another embodiment, the side bend 49 is formed on the mouth segment 52. In another embodiment, the side bend 49 is formed on the pinch tab segment 53. In another embodiment, a combination of side bends 49 and bends 56 are configured and arranged, using conventional spring bending technology, to achieve the desired flow restriction of the tube diameter.

FIG. 9 illustrates a perspective view of an embodiment of the system, wherein the fastener 50 includes a hook 51 which is sized and arranged to connect to an IV stand or another segment of the IV tube 59. The fastener includes a docking wall 76 and a coupling ridge 75. The spring 60 is shown in an uncoupled position. The coupling ridge 75 is sized and configured to seat the spring in a coupled position within the docking wall 76, transitioning to and from an operatively coupled position in the assembly of the system with a desired spring force and a controlled threshold release force, thereby preventing a twisting off below the threshold release force. In another embodiment, angled tab 23 combines with a coupling a ridge 75, or nubbin, and an angle 24. In another embodiment, the fastener 70 includes an aperture 22, a second aperture with a hook 71, and a docking end 33.

As further shown in FIG. 9, the reverse action spring 60 operates by human hand grasping and pinching the top arm 57A and bottom arm 57B simultaneously to open the top end 58A and bottom end 58B. The opening of the reverse action spring 60 creates space to releasably capture the IV tube 59 and does not require preassembly. In this embodiment, the reverse action spring 60 is configured to capture the IV tube 59 and does not have a flow restriction pinch in the uncoupled state. In another embodiment, the reverse action spring 60 pinches the IV tube 59 and creates a flow restriction when in an uncoupled state. In another embodiment, the reverse action spring 60 is replaced with a double wound spring with a mouth segment 52 and a pinch tab segment 53. The reverse action spring 60 is just one example of elements operable in the invention, whereby alternate spring configurations may be operably interchanged without limitation to the scope of the invention.

As further shown in FIG. 9, the fastener contains an integrated electric circuit with one terminal 74A closing a circuit second terminal 74B when the spring ends 58A or 58B bridge the terminals. The internal circuitry is connected to button switch 72 and contained in an electronic housing 73. The button switch 72 will enable toggling between off, armed, and triggered in a notification mode, wherein the circuit will notify the operator when the coupled spring is uncoupled with a notification signal. The power source and circuit components are known in the art and the examples are not limited to embodiments presented. In this embodiment, the power source is a battery. In another embodiment, the power source is a solar cell system. In this embodiment, the notification signal is an LED light. In another embodiment, the notification signal is an audible alarm. In another embodiment, the notification signal is a wireless transmission configured to interact with a computing system and software in the form of a cellular phone. In another embodiment, the circuit includes conventional sensors to indicate a coupled spring, tube, or fastener.

FIG. 10 illustrates a detailed view of an embodiment of the invention's docking features 62, 63, 65, 66, and 67 on a fastener body 64 with the spring 60 shown in a coupled position. The docking tab 63 extends from the fastener body 64 to receive and abut with the top end 58A and bottom end 58B of the spring 60. A ridge 62 is formed to retain the spring in a coupled position until tugged beyond a threshold force. The threshold force is function of variables in spring material, spring diameter, spring configuration, textures and ridge 62 size. A dividing wall 65 and 66 is located symmetrically between the top arm 57A and bottom arm 57B and serves to prevent twisting loose of the spring 60 at a force below the threshold force. A bumper wall 67 is shown on both sides of the spring 60 and is substantially offset from the top arm 57A and bottom arm 57B to allow clearance for the spring 60 as it opens and closes to operatively couples with the fastener body 64, traveling over the ridge 62 to rest on the docking tab 63; and therein transitioning between coupled and uncoupled positions.

As further shown in FIG. 10, a spring 60 is coiled around a pre-assembled tube 61 and retained. By threading a pre-assembled tube 61 through a spring 60 at the manufacturer, and prior to use in the medical site of care, a pre-assembled construct may be quickly erected. An additional segment of in-situ assembled tube 59 is releasably captured in the spring at the medical site of care and does not require pre-assembly. The in-situ assembly requires an additional step to be taken in the field of use, but it also provides added flexibility in collecting slack in tubing and changing out springs or tubes. In the coupled position shown in FIG. 10, the tubes 59 and 61 allow flow of fluids through the lumen 14.

What is claimed is:

1. A tube holding system, comprising:
   a flexible tube defining a lumen and extending between a patient insertion site and an intravenous fluid bag;
   a fastener having a body defining an aperture extending therethrough and a docking end,
   wherein the docking end of the fastener comprises first and second terminals coupled to a circuit housed within the fastener; and
   a spring configured to operatively couple to the docking end of the fastener, the spring comprising a first arm and a second arm opposite the first arm,
   wherein a space between the first arm and the second arm defines a pocket configured to retain the flexible tube,
   wherein the spring and the docking end are movable between a coupled position and an uncoupled position with respect to each other,
   wherein in the coupled position, a first free end of the first arm contacts the first terminal and a second free end of the second arm contacts the second terminal, thereby closing the circuit, and
   wherein in the uncoupled position, the respective first and second free ends are not in contact with the respective first and second terminals, thereby causing the circuit to emit a signal.

2. The system of claim 1, wherein the flexible tube further comprises at least one loop of flexible tube and is retained within the aperture, and wherein the coupled position comprises the at least one loop of flexible tube being affixed to the pocket at a first point and being affixed to the aperture at a second point.

3. The system of claim 1, wherein the docking end comprises a ridge configured to retain the spring in the coupled position at an attachment force threshold.

4. The system of claim 3, comprising an alternate spring configured and arranged to operatively couple to the docking end, and to retain the flexible tube at an alternate attachment force threshold.

5. The system of claim 3, wherein the attachment force threshold exceeds a force of retention threshold between the flexible tube and the aperture.

6. The system of claim 1, wherein the aperture defines a gap, the aperture configured and arranged to form a hook.

7. The system of claim 6, wherein the hook is configured and arranged to attach to a stand.

8. The system of claim 1, wherein the circuit is operatively coupled to an electronic switch configured to enable or disable emission of the signal.

9. The system of claim 1, wherein the spring is color coated to specify a size of the pocket and a force retention threshold.

10. A kit for use in managing medical flexible tube slack, comprising:
    a fastener having a docking end comprising first and second terminals coupled to a circuit housed within the fastener; and a spring configured to operatively couple to the docking end of the fastener, the spring comprising a first arm and a second arm opposite the first arm, wherein a space between the first arm and the second arm of the spring defines a pocket configured to retain a flexible tube, wherein the spring and the fastener are movable between a coupled position and an uncoupled position with respect to each other, wherein in the coupled position, a first free end of the first arm contacts the first terminal and a second free end of the second arm contacts the second terminal, thereby closing the circuit, and wherein in the uncoupled position, the respective first and second free ends are not in contact with the respective first and second terminals, thereby causing the circuit to emit a signal.

\* \* \* \* \*